United States Patent [19]

Davis

[11] 4,203,069
[45] May 13, 1980

[54] METHOD AND APPARATUS FOR NON-DESTRUCTIVELY TESTING ELECTRICALLY CONDUCTIVE ELONGATE CYLINDRICAL COMPONENTS USING AN EDDY CURRENT PRODUCING COIL WITH A ROTOR TO CONCENTRATE THE MAGNETIC FIELD IN A SELECTED AREA

[75] Inventor: Thomas J. Davis, Richland, Wash.

[73] Assignee: Electric Power Research Institute, Inc., Palo Alto, Calif.

[21] Appl. No.: 865,520

[22] Filed: Dec. 29, 1977

[51] Int. Cl.² ............... G01R 33/00; G01N 27/86
[52] U.S. Cl. ................................. 324/220; 324/228
[58] Field of Search ............ 324/219, 220, 221, 228, 324/233, 237, 238, 240, 241242

[56] References Cited

U.S. PATENT DOCUMENTS

| 2,104,646 | 1/1938 | Greenslade | 324/219 |
| 3,152,302 | 10/1964 | Allen et al. | 324/226 |
| 4,002,967 | 1/1977 | Fennell | 324/238 |

FOREIGN PATENT DOCUMENTS 1146771  3/1969  United Kingdom ............ 324/238

Primary Examiner—Rudolph V. Rolinec
Assistant Examiner—Walter E. Snow
Attorney, Agent, or Firm—Flehr, Hohback, Test

[57] ABSTRACT

Method and apparatus for non-destructively testing fabricated metal components with eddy currents. The apparatus includes a coil for generating a magnetic field and means for concentrating the magnetic field into a small inspection volume in the component being tested. The magnetic field induces eddy currents in the component. The coil and the field concentrating means are moved in a manner to scan the component in a predetermined manner with the concentrated eddy currents.

8 Claims, 5 Drawing Figures

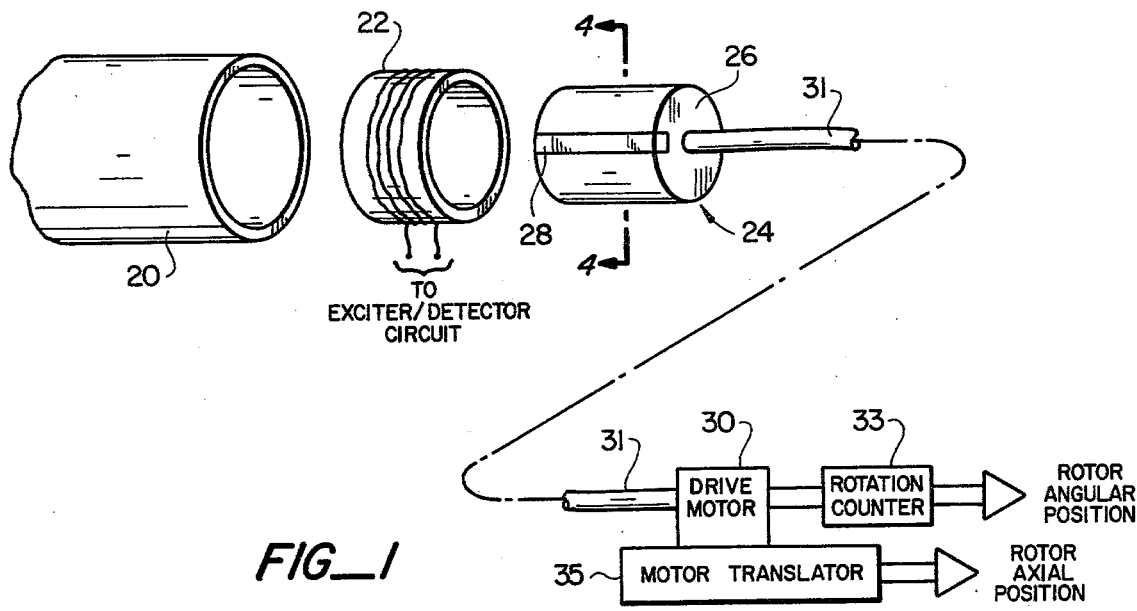
FIG_1
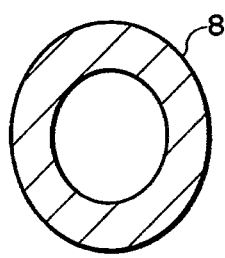
FIG_2
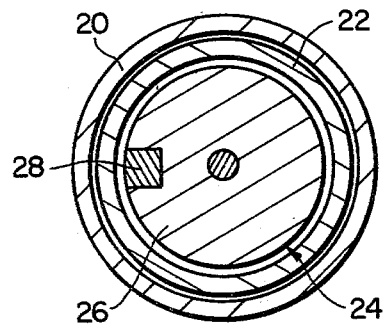
FIG_4
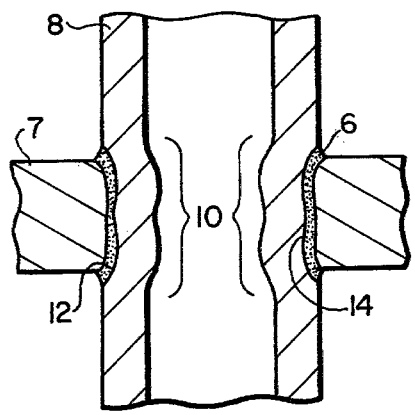
FIG_3
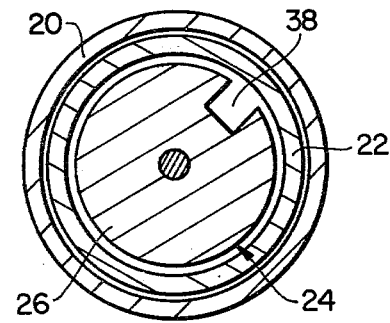
FIG_5

METHOD AND APPARATUS FOR NON-DESTRUCTIVELY TESTING ELECTRICALLY CONDUCTIVE ELONGATE CYLINDRICAL COMPONENTS USING AN EDDY CURRENT PRODUCING COIL WITH A ROTOR TO CONCENTRATE THE MAGNETIC FIELD IN A SELECTED AREA

BACKGROUND OF THE INVENTION

This invention relates generally to techniques for non-destructively testing fabricated metal components and, more particularly, to eddy current inspection systems.

The eddy current method of non-destructively evaluating metal products is widely used as many industries today. The theory and application of this method are described in detail in the "Non-destructive Testing Handbook", R. C. McMaster, editor, Ronald Press, New York, sections 36-38 and 40, 1959.

In the nuclear power industry, however, eddy current inspection has heretofore been unable to test for flaws and incipient defects in the dented regions of steam generator tubes.

Referring to FIGS. 2 and 3, reference numeral 10 indicates the dented region of a typical steam generator tube. The dented region includes the "edge of the dent" 12 which is a zone of transition from the normal tube diameter to the reduced diameter. The edge of the dent occurs near the corners of the tube support 7. The dented region also includes a wrinkle 14 which is a slightly raised area that appears circumferentially around the outside wall of the tube. The wrinkle occurs near the center of the tube support region and can be accompanied by a slightly depressed area on the inner tube wall directly beneath the raised area indicated by reference number 14. From FIG. 2 it can also be seen that denting results in a non-uniform reduction in the diameter of the tube and produces either eliptical or non-circular tubes.

Steam generator tube denting is currently believed to the result of an accumulation of materials 6 between the tube support 7 and the tube 8. These materials are the corrosion products of the accelerated corrosion of the carbon steel support plate 7. During the reactor start up thermal expansion causes a swaging action on the tube which in turn causes a reduction in the diameter of the tube without apparently changing the thickness of the tube wall.

The problem of denting is a very serious concern in the nuclear power industry because the dented regions of steam generator tubes presently cannot be inspected for flaws and incipient defects. Such defects can cause a tube to rupture and result in both a loss of primary coolant from the reactor and the radioactive contamination of the secondary steam system. Cracks and pits are also difficult to detect when located at the edge of a dent 12, beneath a wrinkle 14, near the corner of a tube support 7, or in areas of crud buildup 6. Tube wall thinning or wastage is also difficult to characterize accurately in dented regions.

The currently available eddy current probes used for steam generator tubing inspections cannot adequately characterize the cross-sectional profile of the dented region because of the undesired signals from the tube supports, the variations in diameter, ovality, the build up of curd between the support and the tube and the presence of wrinkles. Currently available eddy current probes are particularly sensitive to variations in tube diameter in the dented region. In addition, severe diameter restrictions and ovality can restrict the passage of standard diameter probes. Further, the signal from a dent can be from twenty to fifty times larger than typical flaw signals. These large signals prevent any characterization of a flaw because the signal processing network is over-driven.

The method currently used for inspecting dents with eddy currents employs a small rotating point coil operating in tandem with a differential encircling coil probe. The differential encircling coil operates in the conventional manner and measures the tube for stress and wastage corrosion. If denting is observed in the tube by the differential coil probe, the dented area is then helically scanned using the small direct contact coil. Such helical scanning is a time consuming process, produces data that is difficult to interpret and extends the time that the nuclear reactor must be shut down. In addition, the electrical signal output from the point coil must be commutated by slip-rings which add to the cost and the noise in the system.

OBJECTS AND SUMMARY OF THE INVENTION

It is an object of the present invention to overcome the problem of accurately testing fabricated components for flaws and defects. In the present invention this problem is solved by an apparatus for scanning fabricated components with concentrated eddy currents.

It is another object of the present invention to detect and measure material variations in thin-walled members. The present invention forms a small eddy current inspection field in the member being measured and this field is manuvered to predetermined positions while measurements are taken.

A further object of the present invention is to accurately measure dents in tubes and to obtain the cross-sectional profile of the dented region, the inside and outside diameters of the tube and the wall thickness of non-circular tubes. The present invention overcomes this measurement problem by scanning the tubes with a magnetic field shaping element in conjunction with an eddy current inducing coil. The magnetic shaping element concentrates the induced eddy currents into a small inspection volume. The inspection volume is sufficiently reduced in size to obtain the desired accuracy and detail.

An additional object of the present invention is to reduce the large signals obtained from dents and from tube supports. The magnetic field shaping means of the present invention reduces the eddy current inspection volume to such a small size that these signal sources can be descriminated against while the flaws and incipient defects can be detected with existing electronic signal processing techniques.

An additional object of the present invention is to provide a high speed helical scanning probe which can be used at conventional translation speeds, resulting in no extension of reactor down-time for inspecting dented tubes.

The foregoing and other objects are achieved by an eddy current inducing coil and a magnetic field shaping means. The coil generates a magnetic field in the component being tested and the field shaping means concentrates the field so that eddy currents are induced in the component in a predetermined inspection volume. The coil and the magnetic field shaping means are moved relative to the component so that the component is scanned in a predetermined manner with concentrated eddy currents.

BRIEF DESCRIPTION OF THE DRAWINGS

FIG. 1, is an exploded and diagramatic view of an apparatus for non-destructively testing components with eddy currents according to the present invention.

FIG. 2, is a cross-sectional view in end elevation of a typical non-circular steam generator tube.

FIG. 3, is a cross-sectional view in side elevation of a typical steam generator tube and its tube support illustrating the problem of denting.

FIG. 4, is a cross-sectional view taken along the line 4—4 of the apparatus of FIG. 1, after assembly and insertion into a tube.

FIG. 5, is a cross-sectional view in end elevation of an alternative embodiment of the present invention.

DESCRIPTION OF THE PREFERRED EMBODIMENTS

Referring to FIG. 1, there is shown an apparatus for non-destructively testing electrically conductive components with eddy currents. Reference numeral 20 indicates a tube being tested by the apparatus. An eddy current inducing coil 22 is inserted into the tube. This coil includes a multi-turn encircling coil wound on a cylindrical coil form which has a diameter less than the inside diameter of the tube 20. The coil is connected to an exciter/detector circuit of known construction. In the preferred embodiment the circuit is a wheatstone bridge eddy current exciter/detector.

A magnetic field shaping means 24, FIG. 1, is inserted into the inducing coil 22. In the preferred embodiment the magnetic field shaping means is a cylindrically shaped rotor comprised of an electrically conductive element 26 and a complementary shaped element having high magnetic permeability 28. The rotor concentrates the magnetic field generated by the coil into a predetermined inspection volume as described below. The conductive portion of the rotor has a generally U-shape and dissipates most of the magnetic field energy coming from adjacent areas of the encircling coil 22. The conductive element is fabricated from high conductivity copper. The magnetically permeable element 28 is rigidly mounted in an axial slot cut in the curved side wall of the rotor. This element is fabricated from ferrite and has a subtended, generally annular cross section as illustrated in FIG. 4. The ferrite element concentrates the eddy currents induced by the coil and not dissipated by the copper element 26 into a correspondingly sized inspection volume in the tube 20. The ferrite element also enhances the magnetic coupling between the coil 22 and the tube 20 and serves to link the eddy current field induced in the tube back to the encircling coil. The combined effect of the copper element 26 and the ferrite element 28 is to render the apparatus sensitive primarily to induced eddy currents located in a volume comparable in the size of the ferrite element and located opposite it within the tube wall.

Referring to FIG. 1, the rotor 24 is rotated about the axis of the tube 20 by a drive motor 30 of known construction. The dive motor is connected to the rotor by a flexible shaft 31. The angular position of the ferrite element 28 in the tube is monitored by a rotation counter 33. The rotation counter generates an electrical signal which thus corresponds to the angular position of the inspection volume in the tube.

The coil 22 and the rotor 24 are moved along the axis of the tube 20 by a translator 35 of known construction. The translator moves the motor 30 which is connected to the rotor and the coil through the flexible shaft 31. For clarity the linkage between the coil and the translator is not shown. The translator also generates an electrical signal indicating the axial position of the rotor in the tube.

In operation the rotor 24 is inserted into the eddy current inducing coil 22 and both are inserted into the tube 20. The coil is excited by a signal generator (not shown) in the exciter/detector wheatstone bridge circuit and generates a time varying magnetic field. The copper portion of the rotor dissipates the magnetic field energy generated from adjacent areas on the excited encircling coil. In the ferrite portion 28 of the rotor the magnetic field is not dissipated and couples to the tube 20 in the area adjacent. The rotor thus concentrates the magnetic field directed at the tube. The time varying magnetic field induces a voltage in the tube which causes eddy currents to circulate in the tube. These eddy currents generate a secondary magnetic field which links back to the encircling coil 22. The secondary field induces a secondary voltage in the coil which causes a change in the voltage-current relationship measured by the wheatstone bridge. In effect, the wheatstone bridge sees a change in the equivalent impedance of the coil 22. The wheatstone bridge is balanced or nulled so that any change in the impedance of the coil is greatly amplified. The output of the bridge circuit is then recorded and displayed by known methods.

To scan the tube, the rotor 24 is turned with respect to the coil 22 and the tube by the drive motor 30. The rotor shapes the magnetic field so that eddy currents are induced in a relatively small inspection volume in the tube. Then the rotor turns, the inspection volume rotates and the rotation counter 33 records its angular position. The rotor 24 and the coil 22 are also moved together axially along the tube 20 by the translator 35. When the rotor and the coil move along the axis of the tube, the inspection volume moves and the translator records its axial position. The tube 20 is scanned in a helical manner by inserting the coil 22 and the rotor 24 into the tube at a uniform rate while simultaneously rotating the rotor 22 with respect to the tube 20.

The measurement is completed by correlating the wheatstone bridge output with the inspection volume position signals.

In one embodiment the rotor 24 was turned at speeds of up to 1400 RPM and inserted to provide an inspection pitch of approximately 0.050 inches. This angular rotation and axial translation provided a translation rate of the probe through the tube of twelve inches per second.

FIG. 5 illustrates an alternative embodiment of the field shaping means of the present invention. In this embodiment an air gap 38 is used in place of the ferrite element. The air gap has substantially zero conductivity and permits the magnetic field lines to occupy their normal position in the gap and to couple energy from the coil 22 into the tube at that position. The result is an area of high eddy current density existing in the tube 20 opposite the air gap. The copper portion of the rotor dissipates the magnetic field as described above and there is a substantially smaller eddy current density around the balance of the circumference of the tube. In effect, the coil 22 is sensitive only to the changes in eddy current density in the volume of the tube opposite the air gap.

The present invention contemplates sizing the magnetic field shaping means to achieve as small an inspection volume as necessary in order to obtain the accuracy required for a valid measurement. In addition, although the preferred embodiments use a generally rectangular slot in the rotor side wall, other configurations are contemplated including trapezoidal and triangular slots.

The present invention also contemplates driving the coil 22 at multiple frequencies. Multiple frequency testing permits an electronic assessment of flaw size since two defect channels can be obtained which are free of probe motion and dent signals. Proper selection of the frequencies of excitation of the coil can establish the independency of the two defect channels so that their ratio or the arc tangent of their ratio can be calibrated to indicate the depths of the flaws.

It should be noted that dent signal elimination with multiple frequency testing is much easier to achieve using the probe of the present invention because the dent signals are comparable in magnitude to defect signals. With conventional probes the sensitivity of the system must be reduced by a factor of twenty to fifty times in order to avoid over driving the system with the dent signal.

Although the preferred embodiment is disclosed above in connection with testing a tube and in particular a dented tube located in a stream generator of a pressurized water nuclear reactor, the present invention contemplates use in any eddy current inspection application. The present invention can be used, for example, to monitor the outside diameter of tubes and to measure flat plates.

It should also be noted that the present invention need not be used exclusively with a wheatstone bridge. Among the other instruments available for use is one that excites the probe with constant current and measures the resulting voltage. Nulling is performed by adding an equal and opposite voltage to the quiescent coil voltage.

Thus, although the best mode contemplated for carrying out the present invention has been herein shown and described, it will be apparent that modification and variation may be made without departing from what is regarded to be the subject matter of the invention.

What is claimed is:

1. Apparatus for non-destructively testing electrically conductive elongate cylindrical components with eddy currents, comprising:
   (a) an eddy current inducing coil for generating a magnetic field which induces eddy currents in the cylindrical component being tested, said coil being generally cylindrical, hollow, and sized for insertion into the component;
   (b) an independently rotatable rotor located inside of and coaxial with the inducing coil, said rotor includes a first member having high electrical conductivity for dissipating in selected areas the magnetic field energy generated by the coil and a second member having high magnetic permeability and located adjacent to the coil for enhancing the magnetic field coupling between the coil and the component being tested, thereby permitting eddy currents to be induced in a selected volume of the component, said first and second members have a generally integral cylindrical shape, said first and second members shape the magnetic field generated by the coil and concentrate the induced eddy currents into a predetermined inspection volume of the component; and
   (c) means for rotating the rotor with respect to the component being tested in a predetermined manner so that the component is non-destructively tested by scanning with concentrated eddy currents.

2. Apparatus for non-destructively testing electrically conductive tubes with eddy currents, comprising:
   (a) an eddy current inducing coil for generating a magnetic field which induces eddy currents in the tube being tested, said coil being generally cylindrical and hollow and having a diameter sized for insertion into the tube being tested;
   (b) an independently rotatable rotor having a solid body, a generally cylindrical shape with a circular cross section and located inside of and coaxial with the inducing coil, said cylindrical rotor having an elongate axial solid member in the side wall thereof and adjacent to the inducing coil, said solid member extends axially along the entire sidewall of the rotor and permits eddy currents to be induced in a selected volume of the tube being tested, said rotor excluding the axial member has high electrical conductivity for dissipating in selected areas the magnetic field energy generated by the coil, said rotor with the axial member thereby shapes the magnetic field generated by the coil and concentrates the induced eddy currents into a predetermined inspection volume of the tube, said rotor being adapted for insertion into the coil and into the tube being tested; and
   (c) means for axially translating the coil and the rotor and for rotating the rotor with respect to the tube being tested in a predetermined manner so that the tube is non-destructively tested by scanning with concentrated eddy currents in a generally helical pattern.

3. The apparatus of claim 2 wherein the solid elongate member has a subtended generally annular cross section and said solid member has conductivity.

4. The apparatus of claim 2 wherein the solid elongate member has a subtended generally annular cross section and said solid member has high magnetic permeability for enhancing the magnetic field coupling between the coil and the component being tested.

5. Method for non-destructively testing electrically conductive cylindrical components with eddy currents, comprising the steps of:
   (a) inserting an eddy current inducing coil into the component being tested, said coil being generally cylindrical and hollow;
   (b) rotating a cylindrical rotor having a cylindrical axis about said axis, and inside of said coil, and with respect to said component, said coil and rotor being co-axial, said rotor includes first means having a solid body with high electrical conductivity for dissipating induced eddy currents and second means in the sidewall of the solid body for permitting eddy currents to be induced in a selected volume of the cylindrical component;
   (c) generating a time varying magnetic field and inducing eddy currents in the component being tested and in the rotor by exciting the eddy current inducing coil;
   (d) concentrating the eddy currents induced in the component in a selected inspection volume with the first and second means of the rotor, said second means permits localized coupling of the time varying magnetic field from the inducing coil into the inspection volume in the component being tested by directing the eddy currents induced in the rotor inward toward the cylindrical axis of the rotor and away from the inducing coil so that the rotor eddy currents adjacent to the second means in the side wall of the rotor do not dissipate said magnetic field at that location and said first means dissipates the remainder of the time varying magnetic field generated by the inducing coil by circulating the rotor eddy currents in the side wall of the rotor adjacent to the inducing coil, said first and second means thereby shape the magnetic field generated by the inducing coil;

scanning the component with the concentrated eddy currents by moving the rotor with respect to the component; and (f) detecting variations in the eddy currents induced in the component.

6. The method of claim 5 wherein the component being tested is a tube and the step of scanning includes:

(a) translating both the eddy current inducing coil and the rotor axially within the tube being tested; and (b) relatively rotating the rotor with respect to the tube being tested so that the tube being tested can be scanned in a helical pattern.

7. Apparatus for non-destructively testing electrically conductive elongate cylindrical components with eddy currents, comprising:

(a) an eddy current inducing coil for generating a magnetic field which induces eddy currents in the cylindrical component being tested, said coil being generally cylindrical, hollow, and sized for insertion into the component;

(b) an independently rotatable rotor having a solid body, a generally cylindrical shape and a generally circular cross section and located inside of and coaxial with the inducing coil, said rotor having a high electrical conductivity for dissipating the magnetic field energy generated by the coil and thereby reducing the induction of eddy currents in selected volumes of the component, said rotor body having an air gap formed by an axial elongate slot in the side wall of the rotor body, said slot extending axially along the entire side wall of the rotor and extending inwardly a predetermined limited distance into the solid rotor body for permitting eddy currents to be induced in a selected volume of the component, said rotor and air gap thereby shape the magnetic field generated by the coil so that the induced eddy currents are concentrated into a predetermined inspection volume of the component; and (c) means for rotating the rotor with respect to the component being tested in a predetermined manner so that the component is non-destructively tested by scanning with concentrated eddy currents.

8. An apparatus as in claim 7 wherein the rotating means includes means for axially translating in a predetermined manner the coil and the rotor with respect to the component being tested so that the component is non-destructively tested by scanning with concentrated eddy currents in a generally helical pattern.

* * * * *